United States Patent [19]

Kaplan

[11] Plant 4,050

[45] May 10, 1977

[54] APPLE TREE

[76] Inventor: Saul L. Kaplan, 916 Greenway Road, Woodbridge, Conn. 06525

[21] Appl. No.: 623,395

[22] Filed: Oct. 17, 1975

[51] Int. Cl.[2] ..... A01H 5/03
[52] U.S. Cl. ..... Plt./34
[58] Field of Search ..... Plt./34

*Primary Examiner*—Edgar S. Burr
*Assistant Examiner*—James R. Feyrer
*Attorney, Agent, or Firm*—DeLio and Montgomery

EXEMPLARY CLAIM

1. A new and distinct variety of apple tree, substantially as herein shown and described, characterized particularly as to novelty by its possession of a unique combination of characteristics, including a laterally branched habit with straighter branches and less tendency to meander than usually found in apple trees, fruit having skin of a deep, rich red color and flesh of an attractive cream color, tender, fine-grained, juicy and having present therein pink flecks adding to usual attractiveness, said characteristics being prevalent essentially before maturity is attained.

1 Drawing Figure

The present invention relates to a new and distinct variety of apple tree which was discovered by me in my cultivated orchard in Woodbridge, Conn., as a result of my pollination, in 1962, of a blossom of the Macoun apple variety with the pollen of a Red Delicious variety.

My new discovery was the result of 25 years of breeding apple trees on my home property and the apple tree which I have now discovered has been asexually reproduced on the same property by grafting on other apple trees of both the Delicious and MacIntosh varieties, whereupon my new variety dominates the understock.

My objectives, in addition to producing a tree and fruit having characteristics considered desirable, such as disease resistance, vigor, annual bearing, productivity and the like, were to develop a tree and fruit with emphasis upon the following:

Fruit having appeal to consumers favoring a sweet juicy apple, crisp at first bite, but readily dissolving in the process of chewing, and with a minimum of fibrous material;

Fruit having a pleasant flavor, as much as 2 weeks before maturity, so as to reduce consumer disappointment resulting from careful attention to proper harvesting; and A tree whose branches tend to grow substantially straight and parallel to the ground to a greater degree than is usually found in apple trees, so that there is improved directional predictability and less need for repetitive pruning.

The accompanying drawing illustrates a typical specimen of the foliage of the apple tree which I have discovered, as borne on a typical branch section. Furthermore, the drawing shows specimens of the fruit, including one specimen shown in cross-section, in color as nearly true as is possible in a color reproduction of this type.

The following is a detailed description of my new variety of apple tree. The source of terminology is "The Apples of New York," Volume I, pages 30–40, by S. A. Beach, N. O. Booth, and O. M. Taylor. This publication is a report of the New York Agricultural Experimental Station.

The color terminology use herein is in accordance with the Maerz and Paul Dictionary of Color as indicated, except where general color terms of ordinary dictionary significance are obvious.

Location where first grown and observed: Woodbridge, Conn.

Dates of first and last pickings: On or about Oct. 1 and Oct. 10, respectively.

Tree: Medium sized; medium vigorous; spreading growth habit; branch crotches tend to be wide-angled within about a 6 foot radius of the trunk of the tree; marked tendency of branches to grow straight, many parallel to ground.

*Trunk.*—Medium stocky, upright.

*Branches.*—Medium thickness, considerable branching; Color — Dark brown after 1 year of growth, subsequently turning dull gray.

*Leaves.*—Medium width and length; oval, pointed; smooth; usually 2½ inches to 3½ inches in length; color — Chrome Green, Plate 23, Hue H-12. Margin — finely serrate.

Flowers:

*Dates of first and full bloom, respectively.*—on or about Apr. 28 and May 5; color: mostly white, with some pink tinge.

Fruit:

*Size.*—Mostly about 2¾ inches to 3 inches in diameter.

*Uniformity.*—Uniform.

*Form.*—Oblate to conic-oblate, symmetrical, quite regular and uniform.

*Stem.*—Mostly medium length, thick or medium thick, not lipped.

*Cavity.*—Acute, medium depth, usually slightly russeted.

*Calyx.*—Nearly convergent; sometimes upright, separated at the base, medium length.

*Basin.*—Medium depth and width, usually slightly ribbed or wavy.

*Skin.*—Medium thickness, tough, without bloom, not waxy or oily.

*Dots.*—Conspicuous, stellar, small and numerous around apex, scattered and large beyond apex, russet color.

*Color.*—Dull dark red blush over entire surface.

Old Burgundy, Plate 56, Hue H-9. None to very faint striping over yellow-green ground color.

*Core lines.*—Meeting.

*Stamens.*—Medium.

*Calyx tube.*—Conical.

*Core.*—Medium, open.

*Carpels.*—Smooth.

Seeds:

*Average number.*—Usually seven, occasionally eight to nine.

*Length.*—Approximately ⅜ inch.

*Breadth.*—About 3/16 inch.

*Color.*—Brown.

*Form.*—Acute, not tufted, plump.

Flesh:

*Color.*—White, tinged with pink at vascular bundles and near skin.

*Firmness.*—Tender, breaking.

*Grain.*—Fine grained.

*Juiciness.*—Juicy.

*Acidity.*—Subacid, more acid than Delicious variety.

*Flavor.*—Mild, pleasant.

*Aroma.*—Not strongly aromatic.

*Sweetness.*—Sweet.

*Quality.*—Very good.

Use of fruit: Market; dessert; sauce-fruit has high sugar content.

I claim:

1. A new and distinct variety of apple tree, substantially as herein shown and described, characterized particularly as to novelty by its possession of a unique combination of characteristics, including a laterally branched habit with straighter branches and less tendency to meander than usually found in apple trees, fruit having skin of a deep, rich red color and flesh of an attractive cream color, tender, fine-grained, juicy and having present therein pink flecks adding to usual attractiveness, said characteristics being prevalent essentially before maturity is attained.

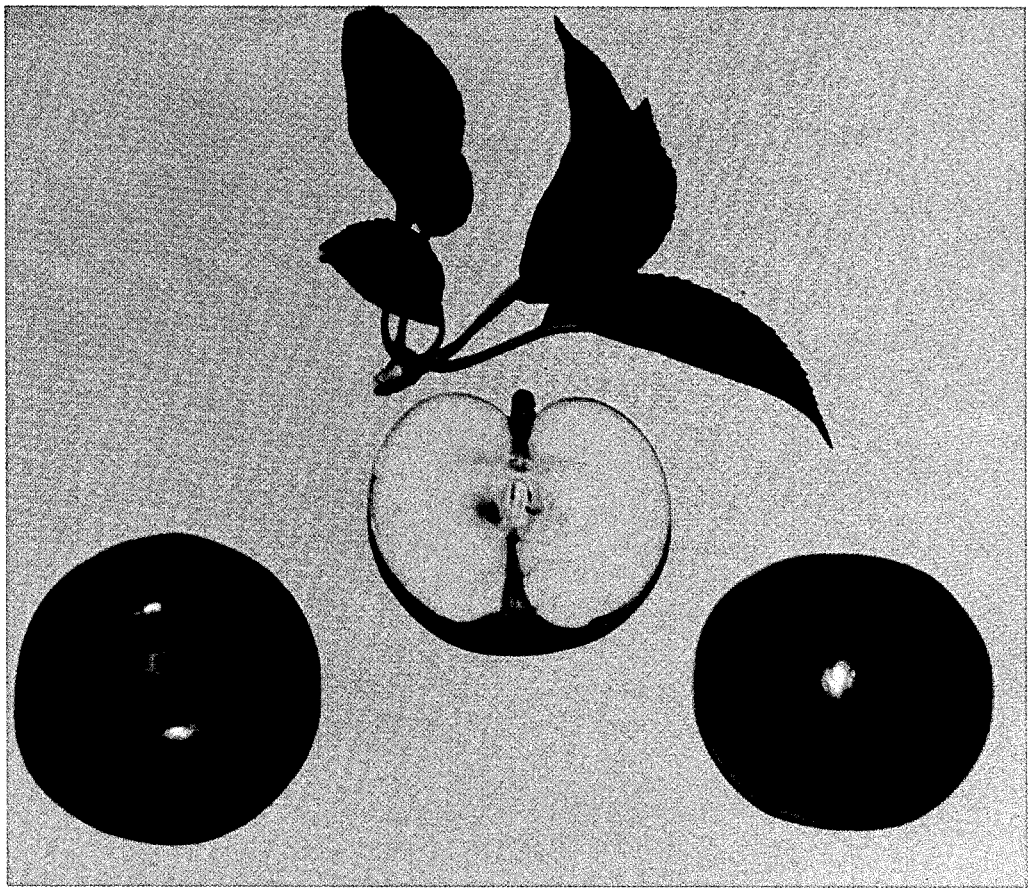

* * * * *